United States Patent
Lee

(10) Patent No.: US 8,656,751 B2
(45) Date of Patent: Feb. 25, 2014

(54) APPARATUS AND METHOD FOR MANUFACTURING IMPLANT USING AMORPHOUS ALLOY

(76) Inventor: Ho Do Lee, Asan-si (KR)

(*) Notice: Subject to any disclaimer, the term of this patent is extended or adjusted under 35 U.S.C. 154(b) by 0 days.

(21) Appl. No.: 13/806,309

(22) PCT Filed: Jun. 20, 2011

(86) PCT No.: PCT/KR2011/004478
§ 371 (c)(1),
(2), (4) Date: Dec. 21, 2012

(87) PCT Pub. No.: WO2011/162512
PCT Pub. Date: Dec. 29, 2011

(65) Prior Publication Data
US 2013/0086967 A1  Apr. 11, 2013

(30) Foreign Application Priority Data
Jun. 23, 2010 (KR) .................. 10-2010-0059423

(51) Int. Cl.
*A61C 8/00* (2006.01)
*A61C 13/08* (2006.01)
(52) U.S. Cl.
USPC ............. 72/364; 72/700; 72/200; 606/151; 623/2.42; 29/522.1; 148/120
(58) Field of Classification Search
USPC .......... 72/128, 342.1, 342.4, 342.6, 364, 200, 72/700; 606/151; 623/2.42, 11.1; 29/522.1; 148/120
See application file for complete search history.

(56) References Cited

U.S. PATENT DOCUMENTS

| | | | | | |
|---|---|---|---|---|---|
| 4,482,402 | A | * | 11/1984 | Taub | 72/128 |
| 4,584,036 | A | * | 4/1986 | Taub et al. | 72/364 |
| 5,896,642 | A | * | 4/1999 | Peker et al. | 29/522.1 |
| 7,887,584 | B2 | * | 2/2011 | Richter | 623/2.42 |
| 7,955,387 | B2 | * | 6/2011 | Richter | 623/11.11 |
| 8,418,516 | B2 | * | 4/2013 | Urakawa et al. | 72/364 |
| 2004/0267349 | A1 | * | 12/2004 | Richter | 606/151 |
| 2009/0317762 | A1 | | 12/2009 | Schiefer et al. | |
| 2011/0202076 | A1 | * | 8/2011 | Richter | 606/151 |

FOREIGN PATENT DOCUMENTS

| | | |
|---|---|---|
| KR | 19927002209 | 9/1992 |
| KR | 1020070051848 | 5/2007 |
| KR | 1020100024975 | 3/2010 |
| WO | 2006017481 | 2/2006 |
| WO | 2010/024541 | * 11/2009 |

OTHER PUBLICATIONS

International Search Report—PCT/KR2011/004478 dated Mar. 5, 2012.

* cited by examiner

*Primary Examiner* — David B Jones
(74) *Attorney, Agent, or Firm* — Cantor Colburn LLP

(57) ABSTRACT

Disclosed are an apparatus and a method for manufacturing an implant having a screw thread on an inner peripheral surface or an outer peripheral surface thereof by die-casting or pressing an amorphous alloy. The apparatus for manufacturing an implant using an amorphous alloy includes: a heating unit for heating a pre-form formed of an amorphous alloy into a semi-solid state; a forming unit for forming a screw thread in the heated pre-form by using a pressing mold; and a cooling unit for cooling the pre-form having the screw thread.

6 Claims, 4 Drawing Sheets

APPARATUS AND METHOD FOR MANUFACTURING IMPLANT USING AMORPHOUS ALLOY

BACKGROUND OF THE INVENTION

1. Field of the Invention

The present invention relates to an apparatus and a method for manufacturing an implant using an amorphous alloy, and more particularly to an apparatus and a method for manufacturing an implant having a screw thread on an inner peripheral surface or an outer peripheral surface thereof by die-casting or pressing an amorphous alloy.

2. Description of the Related Art

In recent years, various materials are being developed due to rapid development of the amorphous alloy material technology.

The amorphous alloy is known to be suitable for biomaterials due to its high hardness, and excellent wear-resistant property and corrosion-resistant property.

Die casting has been developed as a process for forming an amorphous alloy, which corresponds to a method of heating an amorphous alloy, melting the amorphous alloy at a high temperature into a liquid state, injecting the amorphous alloy into a mold, and coagulating the amorphous alloy to form the amorphous alloy.

In the die casting using an amorphous alloy, an atmosphere needs to be controlled in the melting and forming step according to the characteristics of the amorphous material.

That is, an inert gas atmosphere such as argon or a vacuum atmosphere needs to be created.

Thus, in order to form the amorphous alloy through die casting, a separate atmosphere chamber for a melting and forming process is required to satisfy the condition and vertical die casting equipment is applied to stably realize the atmosphere chamber.

However, the vertical die casting apparatus is large-sized and high as compared with its capacity, increasing construction costs.

Further, since an ingot needs to be heated up to approximately 1000 degrees Celsius to be re-melted into a liquid state due to the characteristics of die casting, the apparatus becomes larger and the number of processes increases, increasing process cycle time.

Further, the amorphous alloy is rarely plastically deformed while a mechanical load is applied to the amorphous alloy at room temperature, but behaves resiliently as a whole.

Thus, since a thread machining technology (thread rolling or tapping) utilized in machining of a screw thread of a commercial material (iron, aluminum, and the like) is accompanied by plastic deformation of a surface of the screw thread, it is difficult to apply thread rolling or tapping which is a general thread machining technology to an amorphous alloy which is rarely plastically deformed to form a screw thread.

If a screw thread is formed in an amorphous alloy through thread rolling or tapping, a material or a tool may be damaged, resulting in a failure of the machining.

Meanwhile, a metal implant material used in a human body needs to be a stable material which is not electrically corroded in a linger liquid, and is preferably a material having a high hardness and a high strength by which the material can endure repeated frictions. Mainly, a titanium (Ti) alloy or a Co—Cr based alloy is widely used as the metal implant material.

The titanium (Ta) alloy or the Co—Cr based alloy has excellent mechanical/electrical characteristics, but has a difficulty in being applied to a forming process such as die casting due to its high melting point. Thus, the titanium (Ta) alloy or the Co—Cr based alloy is formed through three-dimensional machining.

However, since the material has excellent mechanical characteristics, it cannot be easily machined. Thus, when a complex three-dimensional shape is to be manufactured, productivity lowers and costs become higher.

It is known that an amorphous alloy such as a Zr—Ti based alloy or a Pd based alloy can be applied to a human body.

Generally, a screw thread is formed on inner and outer peripheral surfaces of a dental or surgical implant, but the method according to the related art has the following disadvantages.

Since it is not easy to machine a screw thread on inner and outer peripheral surfaces of an implant due to a high strength and a high hardness of a titanium (Ti) alloy or a Co—Cr based alloy itself, the price of the implant increases.

Further, when an amorphous alloy is used, a screw thread cannot be formed through thread rolling or tapping due to characteristics of the amorphous alloy, so die casting should be applied. In this case, since it is difficult to design a mold, for example, through setting of a gate such as injection of a molten metal is difficult, it is difficult to secure a surface quality of a screw thread, an apparatus for die casting is high, and it is necessary to re-melt an ingot into a liquid state at a high temperature before the ingot is re-melted, a life span of the mold is significantly shortened and a process cycle time becomes longer.

SUMMARY OF THE INVENTION

Accordingly, the present invention has been made keeping in mind the above problems occurring in the prior art, and an object of the present invention is to provide an apparatus and a method for manufacturing an implant using an amorphous alloy by which an implant having a screw thread on an inner peripheral surface or an outer peripheral surface thereof using an amorphous alloy can be produced promptly at relatively low costs without using die casting.

In accordance with one aspect of the present invention, there is provided an apparatus for manufacturing an implant using an amorphous alloy, the apparatus including: a heating unit for heating a pre-form formed of an amorphous alloy into a semi-solid state; a forming unit for forming a screw thread in the heated pre-form by using a pressing mold; and a cooling unit for cooling the pre-form having the screw thread.

The forming unit may include: a first outer mold an inner surface of which is concavely recessed and having a first screw thread; a first cylinder for moving the first outer mold; a second outer mold coupled to the first outer mold, an inner surface of which is concavely recessed in a direction opposite to the first outer mold, and having a second screw thread; and a cylinder for moving the second outer mold. The pre-form in the heated semi-solid state may be disposed between the first outer mold and the second outer mold and having an external screw thread corresponding to the first screw thread and the second screw thread on an outer peripheral surface of the pre-form, and thermal expansion coefficients of the first outer mold and the second outer mold may be larger than a thermal expansion coefficient of the pre-form.

The forming unit may further include: a core disposed between the first outer mold and the second outer mold and having a third screw thread on an outer peripheral surface thereof; and a third cylinder for elevating the core. The core may be inserted into an inner peripheral recess of the pre-form disposed between the first outer mold and the second outer mold and having an internal screw thread corresponding to the third screw thread on an inner peripheral surface of the pre-form.

The core may be rotated by the third cylinder, and the third cylinder rotates the core inserted into the inner peripheral recess of the pre-form to extract the core from the pre-form.

In accordance with another aspect of the present invention, there is provided a method for manufacturing an implant having a screw thread on an outer peripheral surface or an inner peripheral surface thereof, the method including: a pre-form manufacturing step of manufacturing a pre-form in a state of an ingot by using an amorphous alloy; a heating step of heating the pre-form into a semi-solid state; a disposing step of disposing the pre-form heated into the semi-solid state in a pressing mold for machining of a screw thread; a machining step of forming a screw thread in the heated pre-form by using the pressing mold; and a cooling/separating step of cooling the pre-form having the screw thread and separating the pre-form from the pressing mold, wherein in the heating step, the pre-form is heated to a temperature higher than a glass temperature and lower than a nose temperature, and in the cooling/separating step, the pre-form is cooled below the glass temperature.

In the cooling/separating step, the pressing mold and the pre-form may be separated from each other by using thermal expansion coefficients of the pressing mold and the pre-form.

In the machining step, screw threads may be formed on an outer peripheral surface and an inner peripheral surface of the heated pre-form by using a pressing mold comprising an outer mold surrounding an outer side of the pre-form and a core inserted into the pre-form, and in the cooling/separating step, the core inserted into the pre-form may be rotated to be separated from the pre-form.

As described above, according to the present invention, since an implant having a screw thread on an an inner peripheral surface and/or an outer peripheral surface thereof can be manufactured through pressing instead of die casting by using an amorphous alloy, an implant harmless to a human body can be produced promptly at relatively low costs, improving economical efficiency and productivity.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Figure 1:
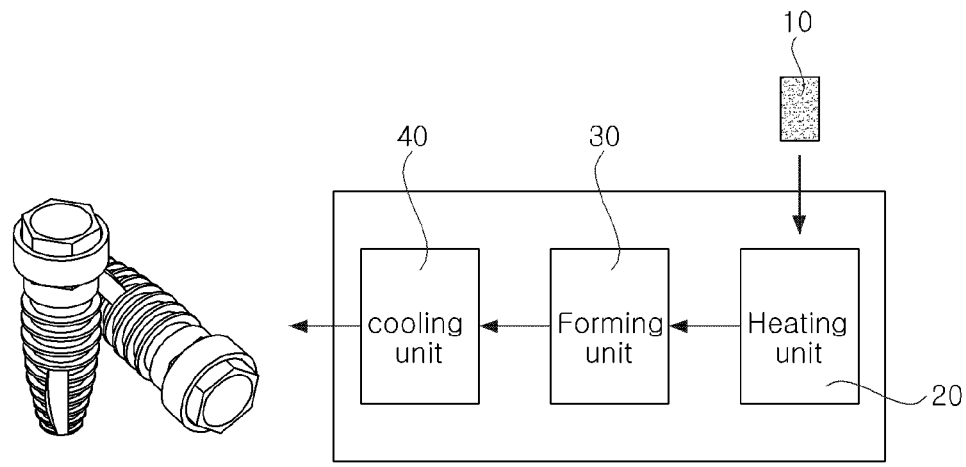
FIG. 1 is a diagram showing an apparatus for manufacturing an implant using an amorphous alloy according to an embodiment of the present invention.
Figure 2:
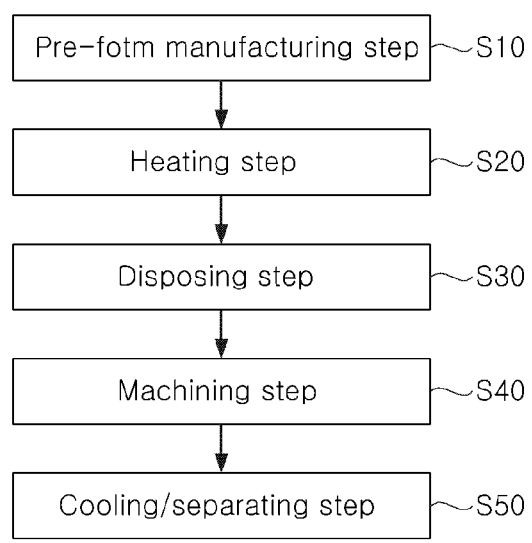
FIG. 2 is a flowchart showing a method for manufacturing an implant using an amorphous alloy according to an embodiment of the present invention.
Figure 3:
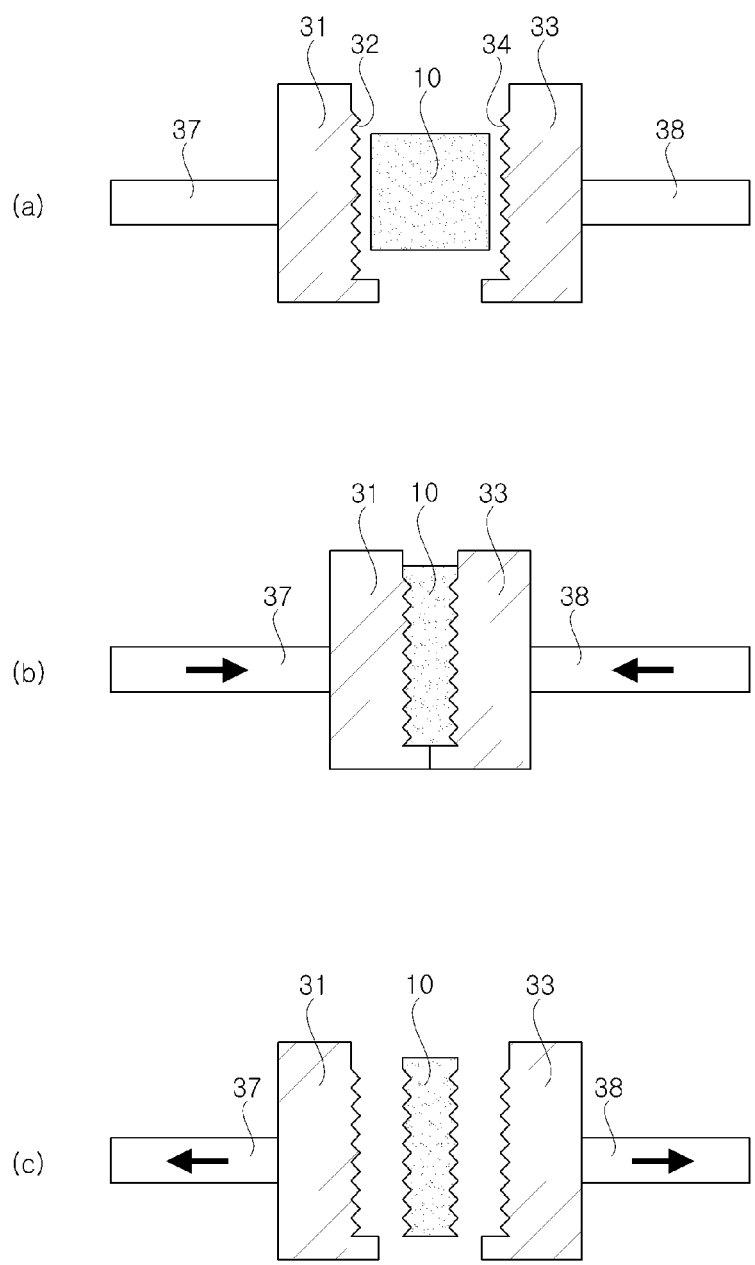
FIG. 3 shows illustrative views of a process of manufacturing an implant having a screw thread on an outer peripheral surface thereof by using the apparatus for manufacturing an implant according to the embodiment of the present invention.
Figure 4:
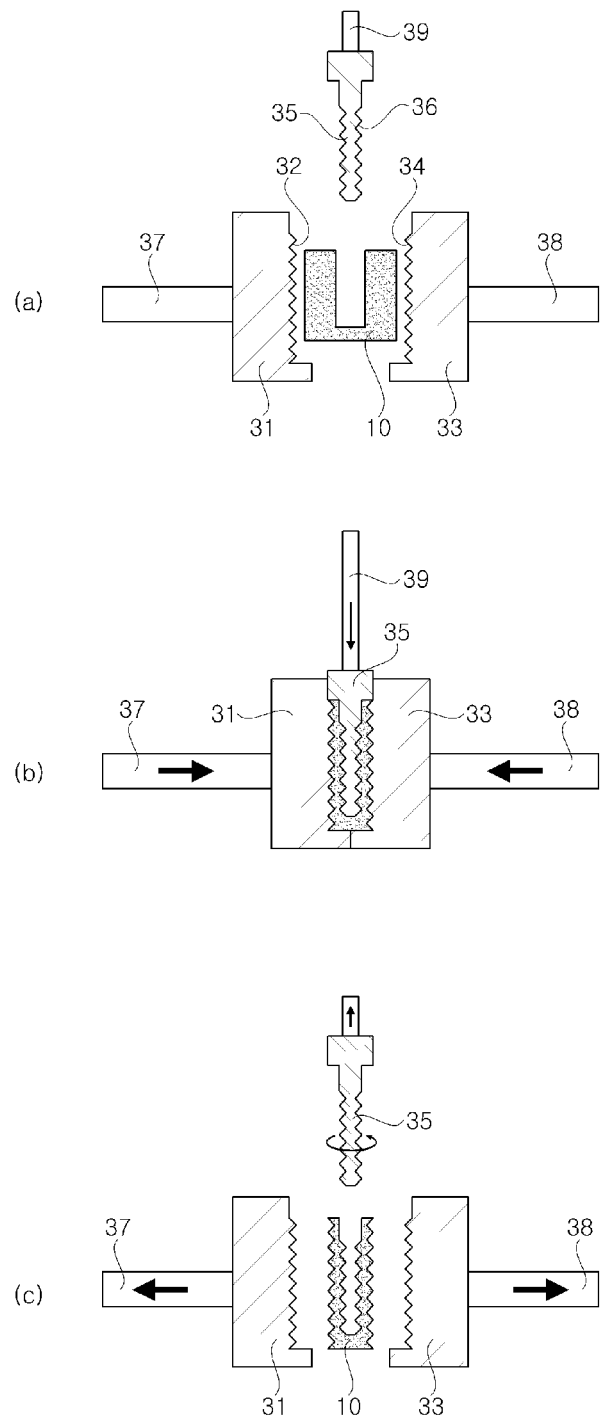
FIG. 4 shows illustrative views of a process of manufacturing an implant having screw threads on inner and outer peripheral surfaces thereof by using the apparatus for manufacturing an implant according to the embodiment of the present invention.
Figure 5:
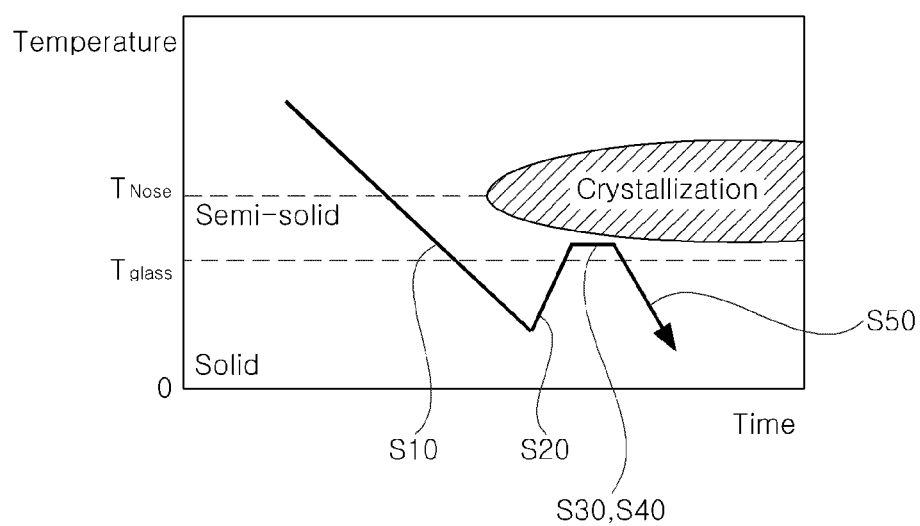
FIG. 5 is a graph showing a thermoplastic forming process according to an embodiment of the present invention.

FIG. 1 is a diagram showing an apparatus for manufacturing an implant using an amorphous alloy according to an embodiment of the present invention. FIG. 2 is a flowchart showing a method for manufacturing an implant using an amorphous alloy according to an embodiment of the present invention. FIG. 3 shows illustrative views of a process of manufacturing an implant having a screw thread on an outer peripheral surface thereof by using the apparatus for manufacturing an implant according to the embodiment of the present invention. FIG. 4 shows illustrative views of a process of manufacturing an implant having screw threads on inner and outer peripheral surfaces thereof by using the apparatus for manufacturing an implant according to the embodiment of the present invention. FIG. 5 is a graph showing a thermoplastic forming process according to an embodiment of the present invention.

The present invention relates to an apparatus and a method for manufacturing an implant in a state in which a pre-form formed of an amorphous alloy is not fused into a liquid state but heated into a semi-solid state.

As shown in FIG. 1, the apparatus for manufacturing an implant using an amorphous alloy of the present invention includes a heating unit 20, a forming unit 30, and a cooling unit 40.

FIG. 1 shows separately the heating unit 20, the forming unit 30, and the cooling unit 40 separately, which may be installed in one unit.

That is, all of heating, forming, and cooling operations may be performed in one unit.

The heating unit 20 functions to heat a pre-form 10 formed of an amorphous alloy into a semi-solid state.

The heating unit 20 heats the pre-form 10 to a temperature higher than a glass temperature Tg shown in FIG. 5 and lower than a nose temperature Tn of the amorphous alloy to convert the pre-form 10 not into a liquid state but into a semi-solid state, that is, a state such as jelly.

The heating unit 20 preheats the pre-form 10 through a method such as high-frequency heating or heating by a heater.

The forming unit 30 functions to form a screw thread on the heated pre-form 10 by using a pressing mold.

As shown in FIG. 3, when a screw thread is to be formed on an outer peripheral surface of the pre-form 10, the forming unit 30 includes a first outer mold 31, a first cylinder 37, a second outer mold 33, and a second cylinder 38.

An inner surface of the first outer mold 31 is concavely recessed to have a first screw thread, and the second outer mold 33 is coupled to the first outer mold 31 and an inner surface of the second outer mold 33 is concavely recessed in a direction opposite to the first outer mold 31 to have a second screw thread 34.

The first cylinder 37 and the second cylinder 38 function to move the first outer mold 31 and the second outer mold 33, respectively.

The pre-form 10 heated into a semi-solid state is disposed between the first outer mold 31 and the second outer mold 33, and an external screw thread corresponding to the first screw thread 32 and the second screw thread 34 is formed on an outer peripheral surface of the pre-form 10.

As shown in FIG. 4, when screw threads are to be formed on an inner surface as well as an outer surface of the pre-form 10, the forming unit 30 further includes a core 35 and a third cylinder 39.

The core 35 is disposed between the first outer mold 31 and the second outer mold 33 and a third screw thread 36 is formed on an outer peripheral surface of the core 35.

The third cylinder 39 functions to elevate the core 35 upward and downward while rotating the core 35.

The core 35 is inserted into an inner peripheral recess of the pre-form 10 disposed between the first outer mold 31 and the second outer mold 33 to form an internal screw thread corresponding to the third screw thread 36 on an inner peripheral surface of the pre-form 10.

The cooling unit 40 cools the pre-form 10 in which a screw thread is formed by the forming unit 30 so that the pre-form 10 can be separated from the pressing mold.

Thermal expansion coefficients of the first outer mold 31 and the second outer mold 33 are preferably larger than a thermal expansion coefficient of the pre-form 10.

That is, when the first and second outer molds 31 and 33 and the pre-form 10 are heated or cooled, the first and second outer molds 31 and 33 are deformed further than the pre-form 10.

Further, the core 35 inserted into the inner peripheral recess of the pre-form 10 is rotated by the third cylinder 39 and extracted from the pre-form 10.

Hereinafter, a method for manufacturing an implant according to the present invention will be described.

The method for manufacturing an implant using an amorphous alloy according to the present invention includes a pre-form manufacturing step S10, a heating step S20, a disposing step S30, a machining step S40, and a cooling/separating step S50.

The pre-form manufacturing step S10 is a step of manufacturing a pre-form 10 in a state of an ingot having a predetermined size and a predetermined shape by using an amorphous alloy.

The heating step S20 is a step of heating the pre-form 10 into a semi-solid state by using the heating unit 20.

As shown in FIG. 5, in the heating step S20, the pre-form 10 is heated to a temperature higher than a glass temperature Tg and lower than a nose temperature Tn of the amorphous alloy.

Accordingly, the pre-form 10 formed of the amorphous alloy is converted into a state in which the pre-form 10 can be plastically machined.

The disposing step S30 is a step of disposing the pre-form 10 heated into a semi-solid state in the forming unit 30 for threading.

In more detail, as shown in FIGS. 3A and 4A, the heated semi-solid state pre-form 10 is disposed between the first outer mold 31 and the second outer mold 33.

Although the pre-form 10 is heated and then is disposed in the forming unit 30 in the embodiment of the present invention, the pre-form 10 may be first disposed in the forming unit 30 and then heated.

The machining step S40 is a step of forming a screw thread in the pre-form 10 disposed between the first outer mold 31 and the second outer mold 33 by the disposing step S30, by using the forming unit 30, that is, the pressing mold.

In the machining step S40, a screw thread is formed only on an outer peripheral surface of the pre-form 10 as shown in FIG. 3B or screw threads are formed on both an outer peripheral surface and an inner peripheral surface of the pre-form 10 as shown in FIG. 4B.

As shown in FIG. 3B, when a screw thread is to be formed only on an outer peripheral surface of the pre-form 10, the first outer mold 31 and the second outer mold 33 are moved to press the pre-form 10 disposed therebetween by using the first cylinder 37 and the second cylinder 38.

Accordingly, an external screw thread corresponding to the first screw thread 32 and the second screw thread 34 are formed on an outer peripheral surface of the pre-form 10.

Further, as shown in FIG. 4B, when screw threads are to be formed on both an inner peripheral surface and an outer peripheral surface of the pre-form 10, the core 35 is first inserted into an inner peripheral recess of the pre-form 10 by using the third cylinder 39, and the first outer mold 31 and the second outer mold 33 are moved to press the pre-form 10 disposed therebetween by using the first cylinder 37 and the second cylinder 38.

Accordingly, an external screw thread corresponding to the first screw thread 32 and the second screw thread 34 is formed on an outer peripheral surface of the pre-form 10, and an internal screw thread corresponding to the third screw thread 36 is formed on an inner peripheral surface of the pre-form 10.

Then, as shown in FIG. 5, since the machining step S40 is performed while the pre-form 10 is heated to a temperature higher than the glass temperature and lower than the nose temperature, the pre-form 10 is plastically deformed to have an external screw thread and/or an internal screw thread.

As shown in FIG. 5, the cooling/separating step S50 is a step of cooling the pre-form 10 having a screw thread below a glass temperature to separate the pre-form 10 from the pressing mold, that is, the forming unit 30.

In the cooling/separating step S50, the pressing mold and the pre-form 10 are separated from each other by using the thermal expansion coefficients of the pressing mold and the pre-form 10.

That is, the thermal expansion coefficients of the first outer mold 31, the second outer mold 33, and the core 35 are larger than the thermal expansion coefficient of the pre-form 10 formed of an amorphous alloy.

Accordingly, if the first outer mold 31, the second outer mold 33, the core 35, and the pre-form 10 are cooled together in the cooling/separating step S50, the first outer mold 31, the second outer mold 33, and the core 35 are contracted further than the pre-form 10, so that the pre-form 10 can be naturally separated form the first outer mold 31, the second outer mold 33, and the core 35.

Thereafter, as shown in FIGS. 3C and 4C, the first outer mold 31 and the second outer mold 33 are moved by using the first cylinder 37 and the second cylinder 38 so that the pre-form having the screw thread, that is, the implant can be extracted.

Further, as shown in FIG. 4, when an internal screw thread is formed on an inner peripheral surface of the pre-form 10 by using the core 35, the core 35 is separated from the pre-form 10 while the core 35 is rotated by using the third cylinder 39 as shown in FIG. 4C, and the first outer mold 31 and the second outer mold 33 are moved to extract the pre-form 10 having an internal screw thread and an external screw thread, that is, the implant.

According to the apparatus and method of the present invention, an implant having a screw thread on an inner peripheral surface and/or an outer peripheral surface thereof can be manufactured of an amorphous alloy by using pressing instead of die casting.

The apparatus and method for manufacturing an implant using an amorphous alloy of the present invention are not limited to the embodiments, but may be variously modified without departing from the spirit of the present invention.

According to the present invention, an implant having a screw thread on an inner peripheral surface and/or an outer peripheral surface thereof can be manufactured of an amorphous alloy by using pressing instead of die casting.

What is claimed is:
1. An apparatus for manufacturing an implant using an amorphous alloy, the apparatus comprising:
   a heating unit for heating a pre-form formed of an amorphous alloy into a semi-solid state;
   a forming unit for forming a screw thread in the heated pre-form by using a pressing mold; and a cooling unit for cooling the pre-form having the screw thread, wherein the forming unit comprises:

a first outer mold an inner surface of which is concavely recessed and having a first screw thread;

a first cylinder for moving the first outer mold;

a second outer mold coupled to the first outer mold, an inner surface of which is concavely recessed in a direction opposite to the first outer mold, and having a second screw thread; and a cylinder for moving the second outer mold, wherein the pre-form in the heated semi-solid state is disposed between the first outer mold and the second outer mold and having an external screw thread corresponding to the first screw thread and the second screw thread on an outer peripheral surface of the pre-form, and thermal expansion coefficients of the first outer mold and the second outer mold are larger than a thermal expansion coefficient of the pre-form.

2. The apparatus of claim 1, wherein the forming unit further comprises:

a core disposed between the first outer mold and the second outer mold and having a third screw thread on an outer peripheral surface thereof; and a third cylinder for elevating the core, wherein the core is inserted into an inner peripheral recess of the pre-form disposed between the first outer mold and the second outer mold and having an internal screw thread corresponding to the third screw thread on an inner peripheral surface of the pre-form.

3. The apparatus of claim 2, wherein the core is rotated by the third cylinder, and the third cylinder rotates the core inserted into the inner peripheral recess of the pre-form to extract the core from the pre-form.

4. A method for manufacturing an implant having a screw thread on an outer peripheral surface or an inner peripheral surface thereof, the method comprising the steps of:

manufacturing a pre-form in a state of an ingot by using an amorphous alloy;

heating the pre-form into a semi-solid state;

disposing the pre-form heated into the semi-solid state in a pressing mold for machining of a screw thread;

forming a screw thread in the heated pre-form by using the pressing mold;

cooling the pre-form having the screw thread; and separating the pre-form from the pressing mold, wherein in the heating step, the pre-form is heated to a temperature higher than a glass temperature and lower than a nose temperature, and in the cooling step and the separating step, the pre-form is cooled below the glass temperature.

5. The method of claim 4, wherein in the cooling step and the separating step, the pressing mold and the pre-form are separated from each other by using thermal expansion coefficients of the pressing mold and the pre-form.

6. The method of claim 4, wherein in the machining step, screw threads are formed on an outer peripheral surface and an inner peripheral surface of the heated pre-form by using a pressing mold comprising an outer mold surrounding an outer side of the pre-form and a core inserted into the pre-form, and in the cooling step and the separating step, the core inserted into the pre-form is rotated to be separated from the pre-form.

* * * * *